(12) United States Patent
Pereira et al.

(10) Patent No.: US 11,241,243 B2
(45) Date of Patent: Feb. 8, 2022

(54) CAPTURE DEVICES AND RELATED METHODS OF USE

(71) Applicant: Boston Scientific Scimed, Inc., Maple Grove, MN (US)

(72) Inventors: Peter J. Pereira, Mendon, MA (US); Martin Phelan, Sussex, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 192 days.

(21) Appl. No.: 16/183,303

(22) Filed: Nov. 7, 2018

(65) Prior Publication Data

US 2019/0133615 A1    May 9, 2019

Related U.S. Application Data

(60) Provisional application No. 62/583,192, filed on Nov. 8, 2017.

(51) Int. Cl.
*A61B 17/22* (2006.01)
*B01D 46/00* (2022.01)
*A61B 10/04* (2006.01)
*A61B 10/00* (2006.01)
(Continued)

(52) U.S. Cl.
CPC .......... *A61B 17/22* (2013.01); *A61B 10/0096* (2013.01); *A61B 10/04* (2013.01); *A61B 17/22031* (2013.01); *B01D 46/0004* (2013.01); *A61B 2017/00296* (2013.01); *A61B 2017/22079* (2013.01); *A61B 2217/005* (2013.01); *A61M 2205/50* (2013.01); *A61M 2205/75* (2013.01); *A61M 2210/1075* (2013.01); *A61M 2210/1078* (2013.01); *A61M 2210/1082* (2013.01);
(Continued)

(58) Field of Classification Search
CPC .............. A61B 17/22; A61B 17/22031; A61B 10/0096; A61B 10/04; A61B 2217/005; B01D 46/0004; B01D 2279/00; A61M 2205/50; A61M 2205/75; A61M 2210/1075; A61M 2210/1078; A61M 2210/1082; B01L 3/502; B01L 2300/0681; B01L 2400/049
See application file for complete search history.

(56) References Cited

U.S. PATENT DOCUMENTS

| | | |
|---|---|---|
| 4,243,040 A | 1/1981 | Beecher |
| 2004/0049152 A1 | 3/2004 | Nayak |
| 2015/0305759 A1 | 10/2015 | St. George et al. |

(Continued)

FOREIGN PATENT DOCUMENTS

| | | | |
|---|---|---|---|
| CN | 204169897 U | 2/2015 | |
| CN | 106937876 A | 7/2017 | |
| EP | 2994295 A1 * | 3/2016 | ............ B29C 70/14 |

*Primary Examiner* — Erich G Herbermann
(74) *Attorney, Agent, or Firm* — Bookoff McAndrews, PLLC (57) ABSTRACT

A system for retrieving material from a cavity in a patient may include a tube having a proximal end and a distal end, the scope configured to be inserted into the cavity, and a filter assembly disposed between the tube and a vacuum source configured to apply negative pressure through the tube to cause the material to flow through the tube from the distal end to the proximal end, the filter assembly including a filter configured to trap the material in the filter assembly, and allow liquid and gases to pass through the filter assembly.

17 Claims, 5 Drawing Sheets

(51) Int. Cl.
*A61B 17/00* (2006.01)
*B01L 3/00* (2006.01)

(52) U.S. Cl.
CPC .......... *B01D 2279/00* (2013.01); *B01L 3/502* (2013.01); *B01L 2300/0681* (2013.01); *B01L 2400/049* (2013.01)

(56) References Cited

U.S. PATENT DOCUMENTS

| | | | |
|---|---|---|---|
| 2016/0022289 A1* | 1/2016 | Wan | A61B 17/221 606/128 |
| 2016/0089185 A1 | 3/2016 | Honda et al. | |
| 2016/0262775 A1 | 9/2016 | Honda | |
| 2017/0224972 A1* | 8/2017 | Ignon | A61M 35/003 |

* cited by examiner

FIG. 10

CAPTURE DEVICES AND RELATED METHODS OF USE

CROSS-REFERENCE TO RELATED APPLICATION(S)

This patent application claims benefit under 35 U.S.C. § 119 to U.S. Provisional Patent Application No. 62/583,192, filed on Nov. 8, 2017, the entirety of which is incorporated herein by reference.

TECHNICAL FIELD

Examples of the present disclosure relate generally to devices to capture material and related methods of use. More particularly, examples of the present disclosure relate to containers and implements for capturing kidney stones with a negative pressure (vacuum) source.

BACKGROUND

Many patients develop stones within their common bile, urinary, renal or ureteral systems. These stones may block ducts and cause great pain and therefore must be removed. Several approaches are available for treating such stones, including, laser treatment to break up the stones into multiple fragments, and subsequent removal of the stones from the body. In some cases, stones are removed from the patient by a basket. However, the use of baskets may be time-consuming, as it may take multiple passes of a basket to capture all of the stones. In other cases, a vacuum can be used. However, vacuum retrieval is subject to clogging of the vacuum lines, particularly when there are significant pressure drops in the system.

Thus, there remains a need for improved methods and devices for capturing and removing kidney stones from the body.

SUMMARY OF THE DISCLOSURE

In one aspect, the disclosure is directed to a system for retrieving material from a cavity in a patient. The system may include a tube having a proximal end and a distal end, the scope configured to be inserted into the cavity, and a filter assembly disposed between the tube and a vacuum source configured to apply negative pressure through the tube to cause the material to flow through the tube from the distal end to the proximal end, the filter assembly including a filter configured to trap the material in the filter assembly, and allow liquid and gases to pass through the filter assembly.

The filter assembly may include a storage housing and a second housing removably coupled to one another, wherein the filter is located in one of the storage housing and the second housing and is configured to retain material having a minimum diameter, and allow liquid, gases, and debris having a diameter less than the minimum diameter to pass through the filter. The system may include at least one end cap for sealing the storage housing after the storage housing is decoupled from the second housing. The filter assembly may include a door movable between a closed configuration and an open configuration, the door enabling a flow of material into the filter assembly in the open configuration, and prohibiting the flow of material into and out of the filter assembly in the closed configuration. The door may be biased into the closed configuration. Application of negative pressure through the filter assembly by the vacuum source may move the door from the closed configuration to the open configuration, and deactivation of the negative pressure through the filter assembly allows the door to move from the open configuration to the closed configuration. The system may include a container disposed between the filter assembly and the vacuum source, wherein the container is configured to capture liquids and solids that pass through the filter of the filter assembly. Any material that passes through the proximal end of the tube must pass through or be retained by the filter assembly. The system may include an attachment removably coupled to the distal end of the tube, and configured to retain material having a diameter larger than a diameter of a lumen of the tube. The attachment may include a door movable between a closed configuration and an open configuration, the door enabling a flow of material into the attachment in the open configuration, and restricting the flow of material into the attachment in the closed configuration. The door of the attachment may be biased into the closed configuration. Application of negative pressure through the attachment by the vacuum source may move the door of the attachment from the closed configuration to the open configuration, and deactivation of the negative pressure through the attachment allows the door of the attachment to move from the open configuration to the closed configuration. The attachment may include a conical trap having a largest diameter at a distalmost point, and a smallest diameter at a proximal most point. The attachment may include a distally-facing surface and a plurality of openings extending through the distally-facing surface. The system may include the vacuum source.

In another aspect, the disclosure is directed to a method of removing material from a patient, the method comprising deploying a tube into a body cavity of the patient, the tube extending from a proximal end toward a distal end, wherein an attachment extends distally from the distal end, the attachment having an internal cavity with a diameter larger than a diameter of a lumen of the tube, applying a negative pressure through the tube to bring material from the body cavity at least partially in the attachment, and withdrawing the tube and the attachment from the body while the one or more kidney stones are disposed at least partially into the attachment.

The attachment may include a door movable between an open configuration and a closed configuration, the door permitting flow of the material into the attachment in the open configuration, and restricting flow of material into the attachment in the closed configuration, and application of the negative pressure through the scope maintains the door in the open configuration.

In yet another aspect, the disclosure is directed to a method of removing material from a patient, the method comprising deploying a tube into a cavity of the patient, applying a negative pressure through the tube to pull the material from the cavity into the distal end of the tube, capturing the material with a filter assembly deployed proximal of the scope, decoupling the filter assembly from the tube, and closing the filter assembly with the material in the filter assembly.

Closing the filter assembly may include closing the filter assembly with one of more caps that are not disposed on the filter assembly during the capturing step. The material may include a kidney stone.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

The accompanying drawings, which are incorporated in and constitute a part of this specification, illustrate several examples of the present disclosure and together with the description, serve to explain the principles of the invention.

DESCRIPTION OF THE EXAMPLES

Reference will now be made in detail to examples of the present disclosure, which are illustrated in the accompanying drawings. Wherever possible, the same reference numbers will be used throughout the drawings to refer to the same or like parts. Both the foregoing general description and the following detailed description are exemplary and explanatory only and are not restrictive of the features, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value.

Examples of the present disclosure include systems, devices, and methods to facilitate, and improve the efficacy and safety of minimally-invasive surgeries. For example, aspects of the present disclosure may relate to medical systems, devices, and methods for providing suction during a medical procedure, such as, for example, a procedure to remove kidney stones or other material from a patient's kidney or other organ or body lumen. In some examples, for example, the medical systems of the present disclosure may include any appropriate insertion sheath and/or any appropriate medical device to deliver treatment to a bodily orifice.

Figure 1:
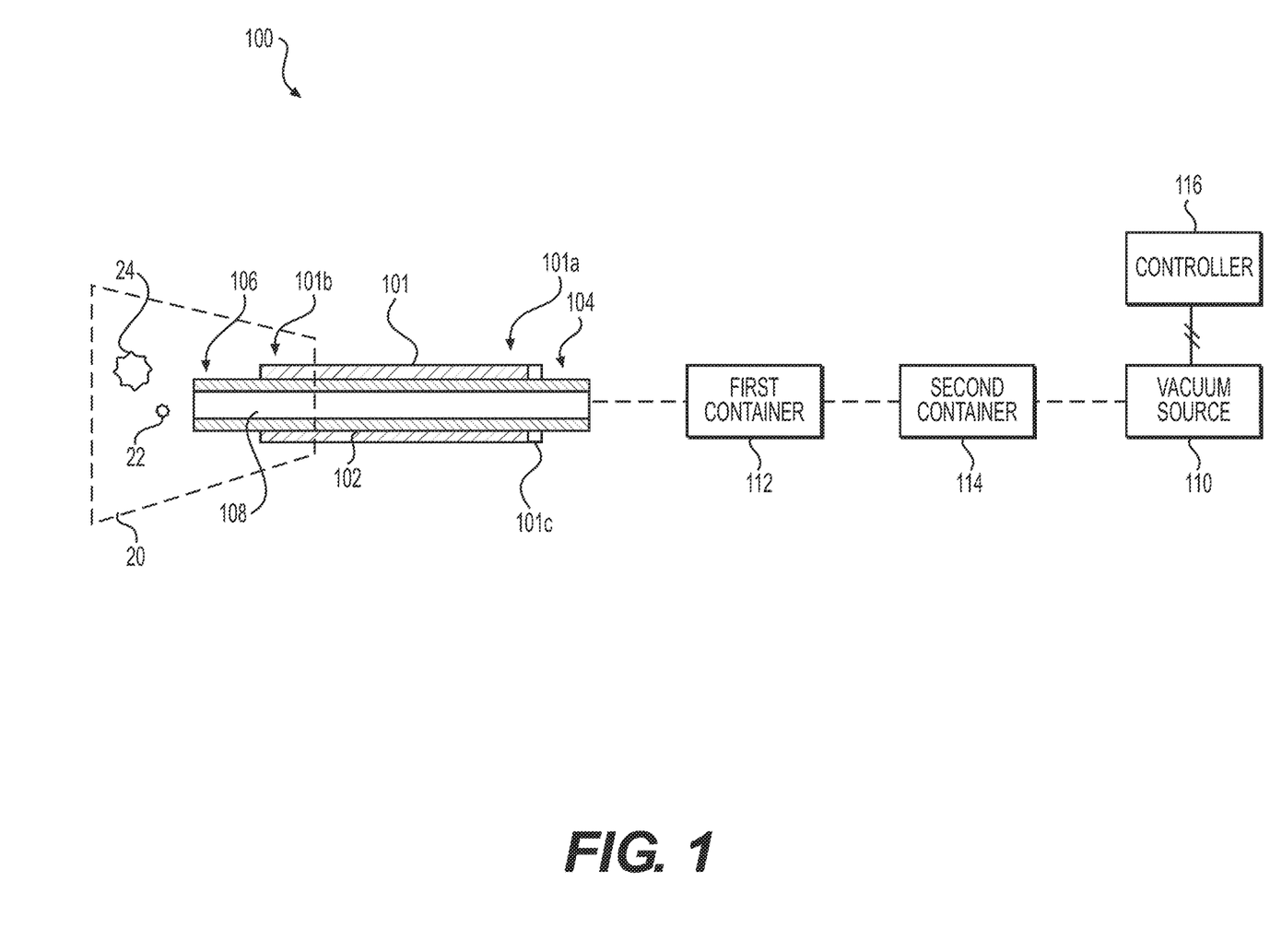
FIG. 1 is a schematic view of a system for capturing kidney stones according to one example of the present disclosure.

FIG. 1 illustrates a medical system 100 that includes an access sheath 101 (shown in cross-section), a tube 102 (also shown in cross-section), and a vacuum source 110. Various containers and/or filters (e.g., first container 112 and second container 114) may be disposed in-line with tube 102 and vacuum source 110. Access sheath 101 may be inserted into a body cavity 20 of a patient to perform medical treatment. Tube 102 may be inserted through access sheath 101 and into body cavity 20. Vacuum source 110 may be configured to provide suction within a lumen 108 of tube 102 and within body cavity 20. Vacuum source 110 may be controlled by a controller 116.

Access sheath 101 may be, for example, a ureteral access sheath (e.g., Navigator™ Ureteral Access Sheath by Boston Scientific Corp.), a renal sheath, a hysteroscope sheath, a cystoscopy sheath, a steerable sheath, or other appropriate access sheath. Access sheath 101 may be formed of an extrusion, and may have various diameters and lengths depending on the medical procedure and body cavity 20. In some aspects, access sheath 101 may include a diameter of approximately 3.66 mm (or 11 French Gauge), a diameter of approximately 4 mm (or 12 French Gauge), a diameter of approximately 4.33 mm (or 13 French Gauge), or another appropriate diameter depending on the medical procedure and body cavity 20. Access sheath 101 may include a hollow lumen extending from a proximal end 101a to an open distal end 101b. Access sheath 101 may include a gasket or seal 101c at proximal end 101a. Tube 102 may be inserted through seal 101c. As shown in FIG. 1, during use, distal end 101b may be positioned within cavity 20, and proximal end 101a may be positioned proximal of cavity 20. Tube 102 may extend distally beyond distal end 101b during use.

Tube 102 may be a hollow, flexible, elongate tube having a proximal end 104, a distal end 106, and one or more lumens 108 extending between proximal end 104 and distal end 106. Tube 102 may be any suitable endoscopic member, such as, e.g., an endoscope, a ureteroscope (e.g., LithoVue™ Single-Use Digital Flexible Ureteroscope by Boston Scientific Corp.), a nephroscope, a colonoscope, a hysteroscope, a uteroscope, a bronchoscope, a cystoscope, a sheath, or a catheter. Tube 102 may include at least one lumen for vacuum suctioning, and may include one or more additional lumens configured for the passage of a variety of surgical equipment, including, but not limited to, imaging devices and tools for irrigation, biopsies, and drug delivery. At least a portion of tube 102 may be radiopaque. Tube 102 may be for single-use and be disposable, or may be sterilized for continued use in different procedures and with different patients (reusable).

Vacuum source 110 may be coupled to tube 102, and configured to draw material (e.g., stones, fluid, other tissue) from outside of distal end 106, through the one or more lumens 108, and out of proximal end 104. Vacuum source 110 (e.g., a vacuum pump, etc.) may provide suction and allow the operator to vary the suction, and may be located near the patient or may be located remotely (such as a vacuum source located on a wall).

Body cavity 20 may be any internal lumen of a patient. For example, body cavity 20 may be a patient's kidney, accessible via the ureter, to remove one or more kidney stones. Alternatively, body cavity 20 may be a patient's colon, accessible via the anus, to remove one or more polyps. In another aspect, body cavity 20 may be a patient's uterus, accessible via the vagina, to remove resected tissue (polyps or fibroids). Body cavity 20 may be a patient's bladder to remove bladder stones, or body cavity 20 may be a patient's vagina to remove or to resect cervical polyps. Body cavity 20 may be any of the aforementioned cavities, and system 100 may be used to remove portions of tumors, cancerous tissue, benign tissue, etc.

System 100 may include one or more containers that are in fluid communication with tube 102 and vacuum source 110. For example, a first container 112 and a second container 114 may be in-line with tube 102 and vacuum source 110. First container 112 may be configured to capture various materials of interest as set forth in further detail below. Filtrate may flow from first container 112 to second container 114, and may remain in second container 114 for disposal or further analysis. In at least some examples, all suctioned solid and liquid material passing through tube 102 will be captured by either first container 112 or second container 114. In other words, at least in some examples, there are no alternative pathways (or bypass) for material to flow from the body into system 100 except through first container 112 and/or second container 114.

Figure 2:
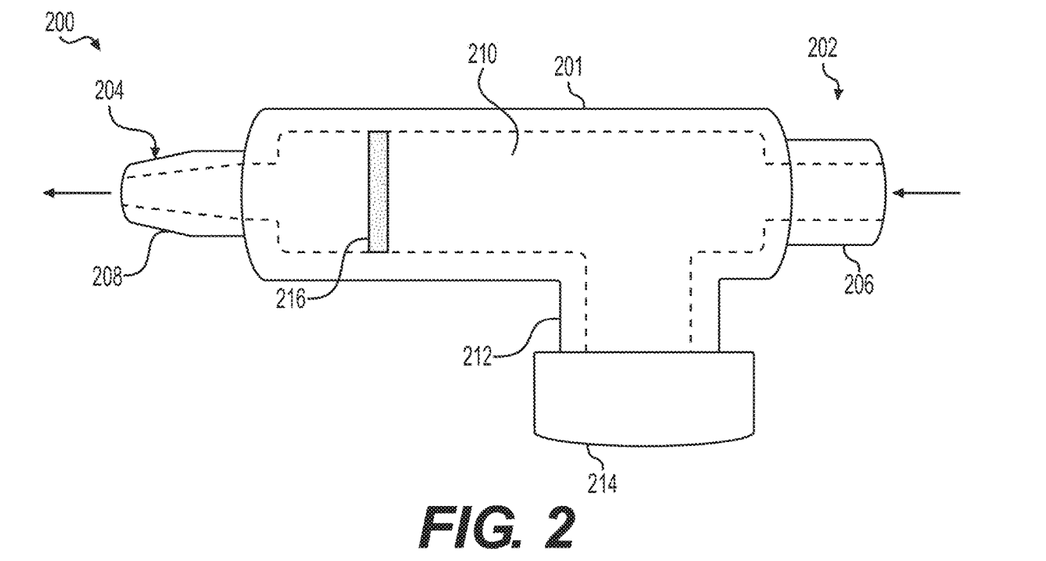
FIG. 2 is a side view of a filter container according to an example of the present disclosure.

Referring to FIG. 2, first container 112 may include a container 200 having a housing 201 that extends from a first end 202 toward a second end 204. The first end 202 may be coupled to proximal end 104 of tube 102 by a connection 206, such as, e.g., a screw-type connection, a snap-fit connection, or the like. Container 200 also may include a connection 208 at second end 204, to which second container 114 and vacuum source 110 (or a line leading to vacuum source 110) may be connected. Container 200 may enclose a cavity or volume 210, through which kidney stones or other materials of interest may be captured and retained. A port 212 may extend substantially perpendicular to a remainder of housing 201, and may be enclosed by a removable cap 214. After one or more kidney stones are captured in volume 210, they may be retrieved by a user through port 212 by removal of cap 214.

A filter 216 may be positioned within volume 210 and may be configured to trap various material (e.g., kidney stones) within volume 210 that are suctioned through tube 102. For example, filter 216 may include a screen, a mesh, a shield, or other suitable barriers configured to capture some materials (such as stones of a desired size), while allowing air, liquid, and smaller particles to pass through. For example, filter 216 may include a metal or plastic mesh configured to trap particles having a minimum diameter (e.g., 0.1-3.0 mm) within volume 210 of first container 112, while allowing particles with a diameter smaller than the minimum diameter to pass through first container 112 to second container 114.

During use, access sheath 101 may be introduced into body cavity 20 of a patient. The user then may insert tube 102 through seal 101c in access sheath 101 and into body cavity 20. Alternatively, tube 102 may be coupled to access sheath 101 (but proximally retracted) when access sheath 101 is inserted into body cavity 20, and tube 102 then may be distally extended. The user may manipulate tube 102 such that distal end 106 is proximate a kidney stone (e.g., kidney stones 22 and 24) or other material to be removed, for example, via a deflection lever, visualization with a camera or fluoroscopy, a guidewire, or other manipulation method.

The user then may, via controller 116, activate vacuum source 110 to remove material from cavity 20. The material, e.g., kidney stones 22 and other bodily fluid and debris, may be sucked with negative pressure through lumen 108. Larger kidney stones 22 and debris may be captured by filter 216 of container 200, while small debris, fluid, and gases may pass through filter 216 and into second container 114. Second container 114 (e.g., a waste container) may store the remaining solid debris and liquid, while gases may be expelled from system 100 through vacuum source 110. Kidney stones or other debris trapped by filter 216 in container 200 may be removed by the user via port 212.

Figure 3:
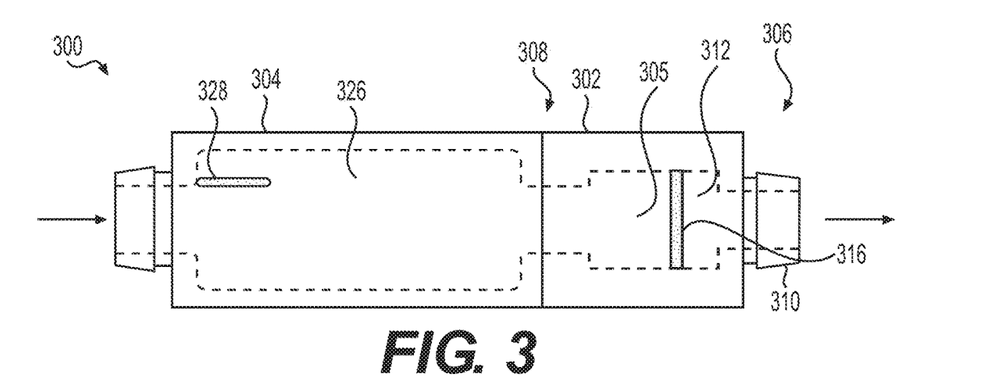
FIGS. 3 and 4 are side views of a filter assembly in assembled and disassembled states according to another example of the present disclosure.
Figure 4:
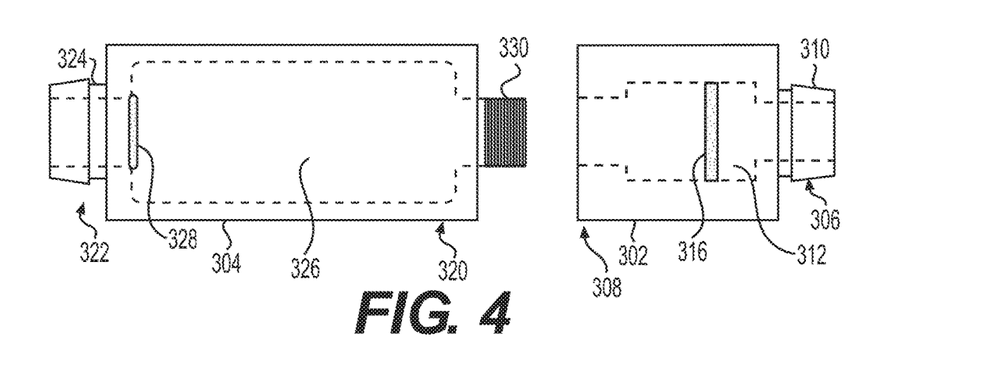
Figure 5:
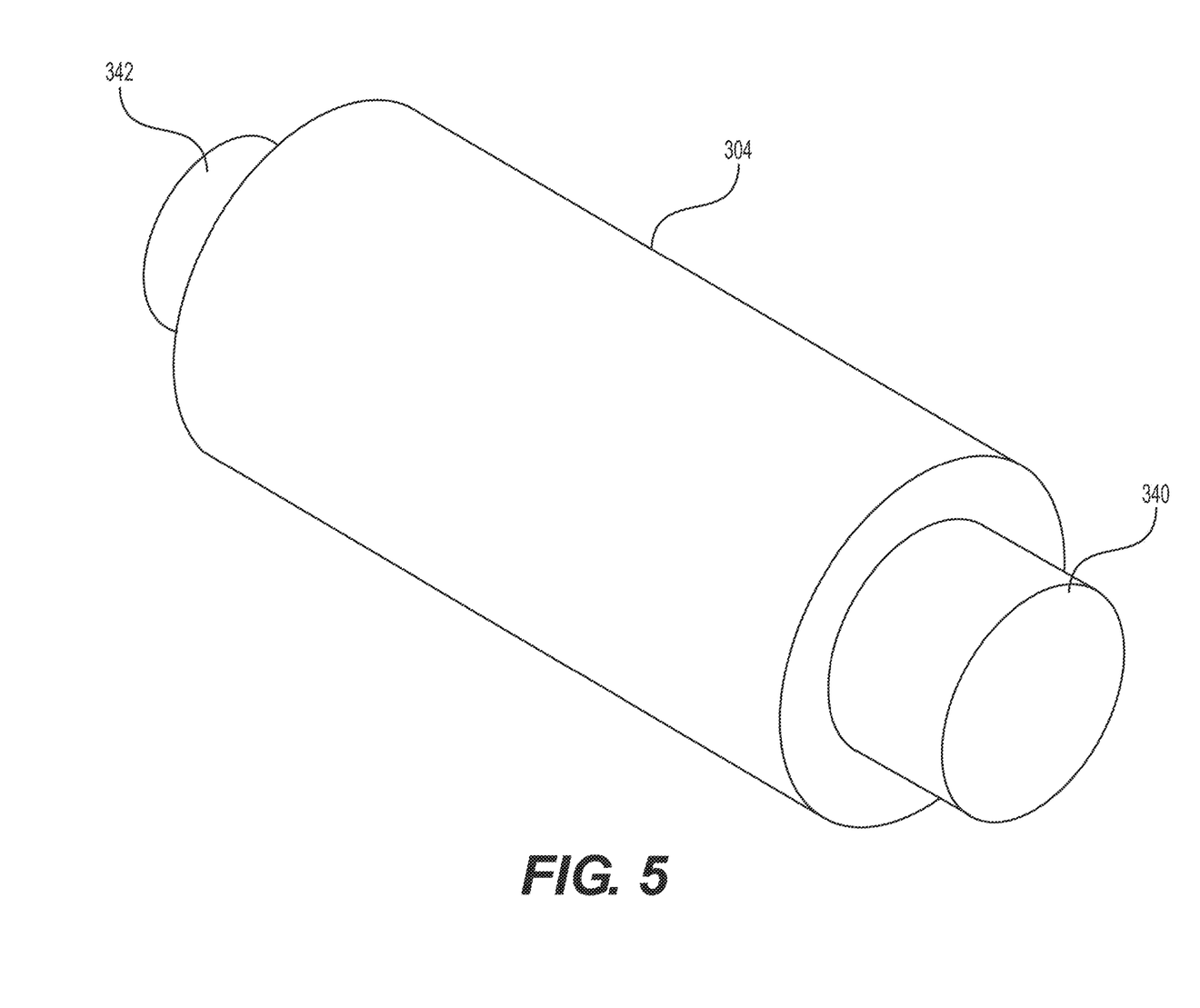
FIG. 5 is a perspective view of a portion of the filter assembly shown in FIGS. 3 and 4.

In another example, first container 112 may include a filter assembly 300 shown in FIGS. 3-5. Filter assembly 300 may include a filter housing 302 and a storage housing 304 that are removably coupled to one another. Filter housing 302 may enclose a cavity or volume 305, and extend from a proximal end 306 toward a distal end 308. A filter 316 that is substantially similar to filter 216 above may be positioned within volume 305. Distal end 308 may include mating features that are complementary to mating features of storage housing 304. In the example shown in FIGS. 3 and 4, distal end 308 may include threads for receiving a threaded connector 330 of storage housing 304, although other suitable connections also are contemplated. A connector 310 may be disposed at proximal end 306, which may be coupled to second container 114 and vacuum source 110 by a conduit (not shown).

Storage housing 304 may extend from a proximal end 320 toward a distal end 322, and may include a cavity or volume 326 for storing kidney stones and the like. A connector 324 at distal end 322 may be configured to mate with or otherwise be fluidly coupled to proximal end 104 of tube 102, and threaded connector 330 may be screwed into complementary threads of filter housing 302. Storage housing 304 also may include a flap or door 328 connected via, e.g., a hinge to an inner surface of storage housing 304. Door 328 may be movable from a closed position (FIG. 4) to an open position (FIG. 3). In the closed position of FIG. 4, door 328 may prevent material from entering or exiting distal end 322 of storage housing 304. It is also contemplated that door 328 may be biased into the closed position via, e.g., a spring, a living hinge, or by a shape memory material in its hinge. Door 326 may partially or entirely cover the opening to volume 326 in the closed configuration. Door 328 may be transitioned to the open position shown in FIG. 3 when a negative pressure is applied through filter assembly 300 by vacuum source 110. That is, the suction force applied by vacuum source 110 may be sufficiently strong to pull door 328 from the closed position to the open position. Door 328 may transition back to the closed position from the open position when suction is no longer being applied by vacuum source 110. In some examples, a filter 316 may be positioned in storage housing 304 (in addition to or as an alternative to the filter 316 shown in FIGS. 3 and 4), and storage housing 304 may be coupled by a conduit to second container 114 without the need for a filter housing 302. Filter 316 also may be positioned more distally within filter housing 302, e.g., at the distalmost point of filter housing 302, so that little or no material accumulates within filter housing 302, and all desired material of sufficient size accumulates within storage housing 304.

Filter assembly 300 also may be positioned in-line with tube 102, second container 114, and vacuum source 110. Filter assembly 300 may be arranged so that storage housing 304 is positioned adjacent to proximal end 104 of tube 102, and so that filter housing 302 is positioned adjacent to second container 114. Suctioned material may flow through storage housing 304 and into filter housing 302, where a filter 316 may trap particles in a substantially similar manner as set forth above with respect to filter 216. Or, as described above, a filter placed within storage housing 304 may trap particles/material. After one or more kidney stones have been removed from a patient, an operator may decouple filter assembly 300 from system 100. Alternatively, housing 302 and/or 304 may remain in line with other system components. Then, an operator may decouple storage housing 304 from filter housing 302. In some examples, this decoupling may be done while storage housing 304 is below filter housing 302 to enable any large stone fragments present within filter housing 302 to fall by gravity into storage housing 304. Yet in other examples, an operator may shake filter assembly 300 before decoupling storage housing 304 and filter housing 302, and while storage housing 304 is below filter housing 302, to cause any stone fragments from filter housing 302 to fall into storage housing 304. Once decoupled, caps 340 and 342 (FIG. 5) may be installed at proximal end 320 and distal end 324 to seal the stone fragments and other large debris in storage housing 304. Storage housing 304 then may be sent to a lab in its sealed state for further analysis of the stone fragments and other debris.

Because storage unit 304 may be sent for subsequent analysis of its contents, a unique identifier, such as a bar code, RFID tag, etc., for sample tracking may be provided on or in storage unit 304. The unique identifier may be permanently associated with storage unit 304 by adhesive label, etching, etc., and may include identifying information that may be associated with the patient in an electronic database. The unique identifier, filter housing 302, and/or storage housing 304 may be reusable for at least the same patient.

Figure 6:
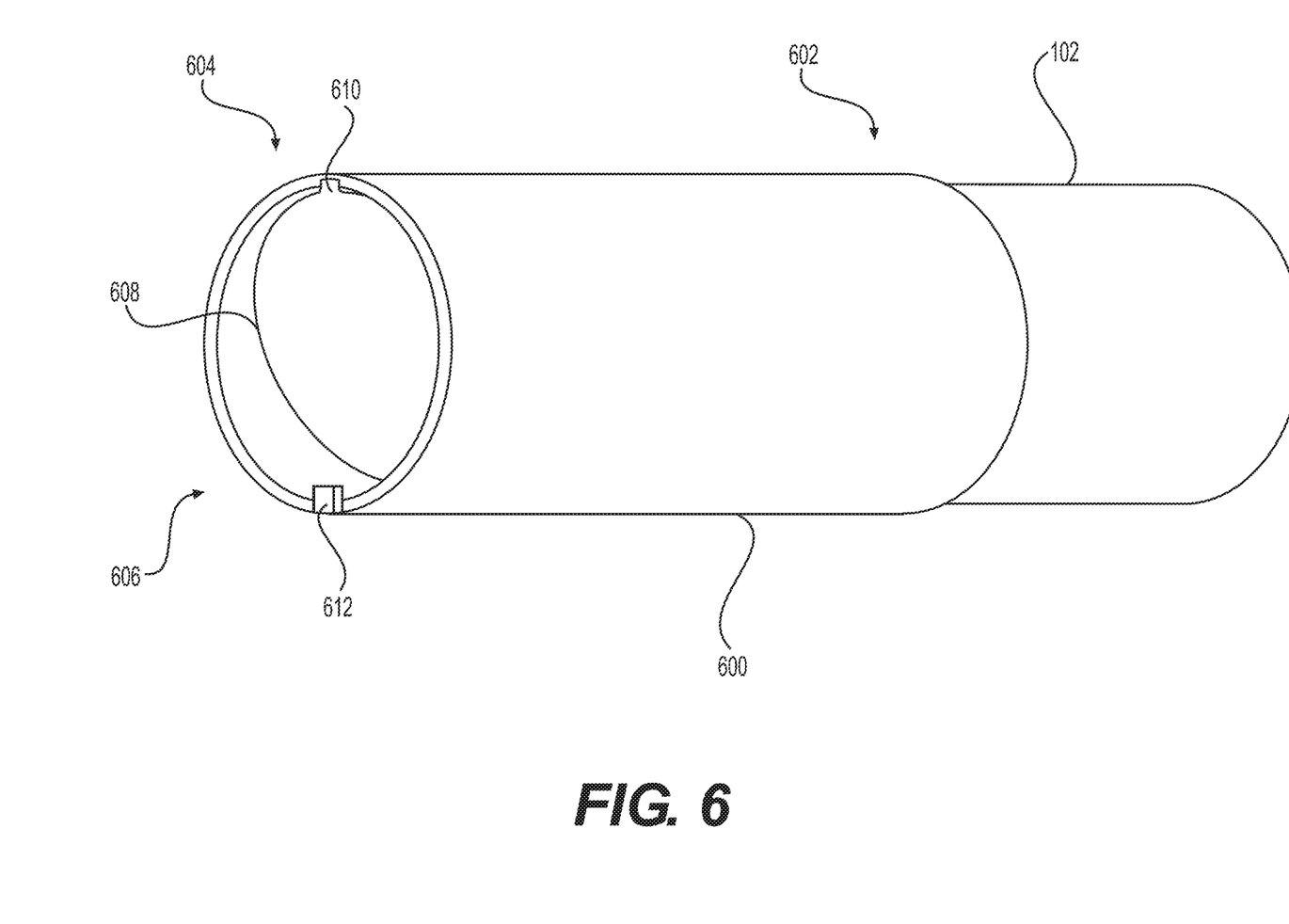
FIG. 6 is a perspective view of an endoscopic attachment for capturing kidney stones according to another example of the present disclosure.

FIGS. 6-10 show various implements that may be attached to the distal end of a scope or other catheter, e.g., tube 102, and used to collect kidney stones or other objects or material in the body. Referring to FIG. 6, attachment 600 may be generally cylindrical in shape (although other shapes are also contemplated), and may extend from a proximal end 602 toward a distal end 604. Proximal end 602 may include various features for securing to the distal end of tube 102, including, e.g., clips, brackets, friction, detent, thread, magnet, mating features, and the like. In some examples, an attachment kit may be included with attachment 600 that can be used to modify the distal end of tube 102. In other examples, tube 102 may be preformed with corresponding attachment features for securing attachment 600. Attachment 600 also may include a distally-facing opening 606 through which kidney stones, other debris, and fluids may enter an internal cavity or volume of attachment 606.

Attachment 600 also may include a flap or door 608 connected via, e.g., a hinge 610 to a surface of attachment 600. Door 608 may be movable from a closed position to an open position in a substantially similar manner as set forth above with respect to door 328 of FIGS. 3 and 4. In other embodiments, however, attachment 600 may not include any flap or door. In such embodiments, vacuum source 110 may remain on during collection of stones and other biologic material. In particular, once one or more stones is received in the internal cavity of attachment 600, vacuum source 110 may remain active during withdrawal of attachment 600 form the body to retain the stones in attachment 600. Still further, larger stones, e.g., stones having a diameter larger than the diameter of opening 606 may be more easily retained when attachment 600 does not include a flap or door covering opening 606.

In the closed position, door 608 may prevent material from entering or exiting opening 606 of attachment 600. It is also contemplated that door 608 may be biased into the closed position via, e.g., a spring or by a shape memory material in its hinge. In the closed position, door 608 may cover a portion or an entirety of opening 606. Door 608 may be transitioned to the open position when a negative pressure is applied by vacuum source 110. That is, the suction force applied by vacuum source 110 may be sufficiently strong to pull door 608 from the closed position to the open position. Door 608 may transition back to the closed position from the open position when suction is no longer being applied by vacuum source 110. A stop 612 disposed distally of door 608 may prevent door 608 from surging distally past distal opening 606 of attachment 600.

Tube 102 and attachment 600 may be extended into cavity 20 through access sheath 101 (FIG. 1), and positioned adjacent to a kidney stone or other material desired to be moved. The user then may, via controller 116, activate vacuum source 110 to remove material from cavity 20. The material, e.g., kidney stones 22 and other bodily fluid and debris, may be sucked with negative pressure through opening 606 into the internal volume of attachment 600. Some kidney stones 22 may be small enough to fit through lumen 108 (FIG. 1) of tube 102 and into first container 112 and/or second container 114. Other stones, however, may be too large to travel through lumen 108. Depending on their size, these larger stones may be completely or partially contained within the internal volume of attachment 600. For example, kidney stones having a diameter smaller than opening 606, but larger than lumen 108 may be retained within the internal volume of attachment 606. Once a procedure is completed, or if a blockage or clog is detected, vacuum source 110 may be powered down. The cessation of negative pressure through the system may allow or cause door 608 to close, securing the larger stones within the cavity of attachment 606. Then, tube 102 and attachment 600 may be removed from body cavity 20 so that the kidney stones secured in attachment 600 may be removed and/or so that any other blockages may be cleared. Attachment 600 may include one or more caps, e.g., similar to caps 340 and 342 of FIG. 5, so that after a procedure has been performed, attachment 600 can be sealed and sent to a lab for analysis of the acquired material.

In other examples, tube 102 and attachment 600 may be withdrawn from body cavity 20 while vacuum source 110 is still active. This withdrawal mechanism may be advantageous when a kidney stone is relatively large and cannot be entirely contained within attachment 600. It may also be advantageous, in some embodiments, for attachment 600 not to have any closure, e.g., door 608) at its distal end, so as to accommodate larger material. Such larger material or kidney stones (e.g., having a diameter larger than the diameter of opening 606) may be lodged in opening 606. However, due to the application of negative pressure from vacuum source 110, the larger stone may remain lodged within the opening, or may remain otherwise secured to attachment 600, so that the entire larger stone can be removed from the body by withdrawing tube 102.

Figure 7:
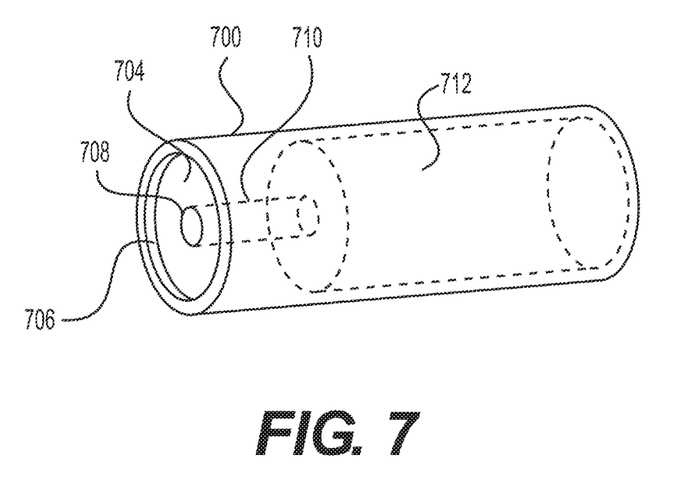
FIGS. 7-10 are perspective views of alternative endoscopic attachments.

FIGS. 7-10 show alternative attachments for use with tube 102. An attachment 700 is shown in FIG. 7 having a distally-facing surface 704 and a circumferential rim 706 that extends distally from surface 704. Surface 704 may include an opening 708 coupled to a lumen 710, through which suction may be applied. Lumen 710 may be coupled to an internal cavity or volume 712 of attachment 700. Internal volume 712 may have a larger diameter than lumen 710 to enable volume 712 to receive the distal end of tube 102, and accumulate stones or other material. The smaller lumen 710 restricts the collection of stones to stones of only a sufficiently small size to prevent clogging of tube 102 or other parts of the system.

Figure 8:
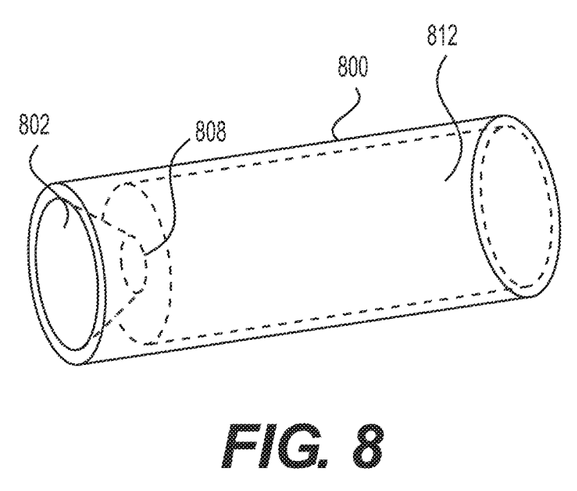

An attachment 800 is shown in FIG. 8 having a conical trap 802 at its distal end. Conical trap 802 may be recessed radially inward moving in the proximal direction. That is, conical trap 802 may have a largest diameter at its distalmost point, and a smallest diameter at its proximalmost point. Conical trap 802 may include an opening 808 coupled to an internal volume 812 of attachment 800. Attachment 800 may have the same advantage discussed above with respect to FIG. 7. Trap 802 also may have the advantage of holding stones larger than opening 808 but smaller than the distal opening of conical trap 802. Upon removal of that stone, while suction is applied, the stone will not bear against other surfaces of a body lumen or a lumen of a scope, helping to prevent injury or damage to the body lumen and/or scope.

Figure 9:
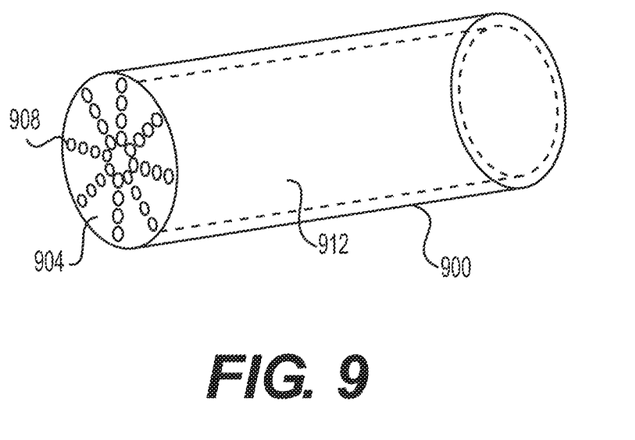
Figure 10:
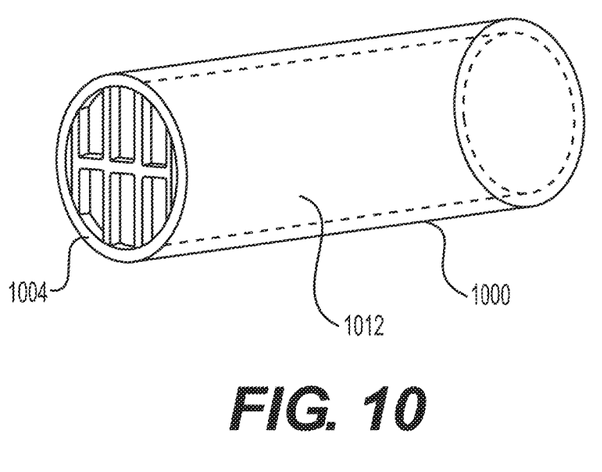

An attachment 900 is shown in FIG. 9 having a distally-facing surface 904 and a plurality of openings 908 extending through surface 904 in a spoke pattern. Alternatively, openings 908 may be arranged in other patterns, other hole shapes, and other number of holes on surface 904. Openings 908 may be in communication with an internal cavity or volume 912 of attachment 900. An attachment 1000 is shown in FIG. 10 having a grate trap 1004 at its distal end. The openings of the grate trap 1004 may be in communication with an internal cavity or volume 1012 of attachment 1000. FIGS. 9 and 10 may have the same advantage discussed above with respect to FIG. 7.

Also, at least some of the embodiments of FIGS. 7-10 allow a lithotripter or other like device therethrough to break up large stones into smaller fragments. Still further, the embodiments of FIGS. 7-10 may allow stones to be captured and retained in the respective attachments to some extent, and may allow for the separation of differently sized kidney stones for sorting purposes or targeting of certain sized stones for analysis. Since the size of the various openings are known, these designs may provide size-sorting pathways allowing the physician to select a range of stones to retrieve.

Examples of the present disclosure may help prevent clogging of suction lumens while also enabling the easy removal of kidney stones and other debris from a patient. The use of the disclosed examples may reduce the number of kidney stones that must be fragmented by, e.g., laser lithotripsy, before being removed from the patient, and also may reduce overall procedure time by removing stones and stone fragments at a faster rate than existing methods and devices. Additionally, the use of the attachments described in FIGS. 6-10 may allow for time-efficient removal of relatively large kidney stones, and without any fragmentation in some cases.

While much of this disclosure is directed to ureteroscopic kidney stone removal, it is further contemplated that the systems and procedures discussed herein may be equally applicable to other material removal procedures. For example, the systems, devices, and methods discussed above may be used during a percutaneous nephrolithotomy/nephrolithotripsy (PCNL). The systems, devices, and methods discussed above also may be used in procedures to remove ureteral stones, gallstones, bile duct stones, polyps, fibroids, tumors, cancerous tissue, or any other biologic or non-biologic material.

Other examples of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A system for retrieving material from a cavity in a patient, comprising:
    a tube having a proximal end and a distal end, the tube configured to be inserted into the cavity; and
    a filter assembly disposed between the tube and a vacuum source configured to apply negative pressure through the tube to cause the material to flow through the tube from the distal end to the proximal end, the filter assembly including a filter configured to trap the material in the filter assembly, and allow liquid and gases to pass through the filter assembly,
    wherein the filter assembly includes a storage housing and a second housing removably coupled to one another, the filter assembly is linearly aligned with the tube and the vacuum source, and the filter assembly is a straight linear structure,
    wherein the filter is located in the storage housing but not the second housing or the filter is located in the second housing but not the storage housing, and the filter is configured to retain material having a minimum diameter, and allow liquid, gases, and debris having a diameter less than the minimum diameter to pass through the filter.

2. The system of claim 1, further including at least one end cap for sealing the storage housing after the storage housing is decoupled from the second housing.

3. The system of claim 1, wherein the filter assembly includes a door movable between a closed configuration and an open configuration, the door enabling a flow of material into the filter assembly in the open configuration, and prohibiting the flow of material into and out of the filter assembly in the closed configuration.

4. The system of claim 3, wherein the door is biased into the closed configuration.

5. The system of claim 3, wherein application of negative pressure through the filter assembly by the vacuum source moves the door from the closed configuration to the open configuration, and deactivation of the negative pressure through the filter assembly allows the door to move from the open configuration to the closed configuration.

6. The system of claim 1, further including a container disposed between the filter assembly and the vacuum source, wherein the container is configured to capture liquids and solids that pass through the filter of the filter assembly.

7. The system of claim 1, wherein any material that passes through the proximal end of the tube must pass through or be retained by the filter assembly.

8. The system of claim 1, further including an attachment removably coupled to the distal end of the tube, and configured to retain material having a diameter larger than a diameter of a lumen of the tube.

9. The system of claim 8, wherein the attachment includes a door movable between a closed configuration and an open configuration, the door enabling a flow of material into the attachment in the open configuration, and restricting the flow of material into the attachment in the closed configuration.

10. The system of claim 9, wherein the door of the attachment is biased into the closed configuration.

11. The system of claim 9, wherein application of negative pressure through the attachment by the vacuum source moves the door of the attachment from the closed configuration to the open configuration, and deactivation of the negative pressure through the attachment allows the door of the attachment to move from the open configuration to the closed configuration.

12. The system of claim 8, wherein the attachment includes a conical trap having a largest diameter at a distalmost point, and a smallest diameter at a proximalmost point.

13. The system of claim 8, wherein the attachment includes a distally-facing surface and a plurality of openings extending through the distally-facing surface.

14. The system of claim 1, further comprising the vacuum source.

15. A system for retrieving material from a cavity in a patient, comprising: a tube having a proximal end and a distal end, the distal end of the tube configured to be inserted into the cavity; a filter assembly disposed between the tube and a vacuum source configured to apply negative pressure through the tube to cause the material to flow through the tube from the distal end to the proximal end, the filter assembly including a filter configured to trap the material in the filter assembly, and allow liquid and gases to pass through the filter assembly; and an attachment removably coupled to a distalmost end of the tube, the attachment including a conical trap having a largest diameter at a distalmost point, and a smallest diameter at a proximalmost point; wherein the filter assembly includes a storage housing and a second housing removably coupled and linearly aligned to one another such that the material may flow linearly from a distal end of the storage housing to a distal end of the second housing, and wherein the filter is located in the storage housing but not the second housing or the fitter is located in the second housing but not the storage housing and wherein the filter assembly is a straight linear structure.

16. The system of claim 15, further comprising a second housing between the filter assembly and the vacuum source, wherein the second housing is configured to retain the liquid and gases passing through the filter assembly.

17. The system of claim 15, wherein the tube consists of a proximal end and a distal end.

* * * * *